(12) United States Patent
Sullivan

(10) Patent No.: US 6,782,887 B2
(45) Date of Patent: *Aug. 31, 2004

(54) MEDICAMENT RESPIRATORY DELIVERY DEVICE AND CARTRIDGE

(75) Inventor: Vincent Sullivan, Morrisville, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 131 days.

This patent is subject to a terminal disclaimer.

(21) Appl. No.: 10/141,849

(22) Filed: May 10, 2002

(65) Prior Publication Data

US 2004/0011356 A1 Jan. 22, 2004

Related U.S. Application Data

(63) Continuation-in-part of application No. 09/879,517, filed on Jun. 12, 2001, which is a continuation-in-part of application No. 09/758,776, filed on Jan. 12, 2001.

(51) Int. Cl.[7] .............................................. A61M 15/00
(52) U.S. Cl. ........................... 128/203.15; 128/200.14; 128/200.23; 128/203.21
(58) Field of Search ...................... 128/200.14, 200.23, 128/203.15, 203.21

(56) References Cited

U.S. PATENT DOCUMENTS

| 3,949,751 | A | * | 4/1976 | Birch et al. ............ 128/203.15 |
| 5,215,221 | A | * | 6/1993 | Dirksing ....................... 222/94 |
| 5,619,984 | A | * | 4/1997 | Hodson et al. ......... 128/203.15 |
| 5,702,362 | A | * | 12/1997 | Herold et al. ................. 604/58 |
| 5,921,236 | A | * | 7/1999 | Ohki et al. ............ 128/203.15 |
| 5,941,867 | A | * | 8/1999 | Kao ........................... 604/416 |
| 6,443,152 | B1 | * | 9/2002 | Lockhart et al. ....... 128/203.21 |
| 6,606,992 | B1 | * | 8/2003 | Schuler et al. ......... 128/203.15 |
| 6,644,309 | B2 | * | 11/2003 | Casper et al. .......... 128/203.21 |
| 6,655,379 | B2 | * | 12/2003 | Clark et al. ............ 128/203.12 |
| 6,722,364 | B2 | * | 4/2004 | Connelly et al. ...... 128/203.15 |

FOREIGN PATENT DOCUMENTS

WO        WO 02/055133 A2      7/2002

* cited by examiner

Primary Examiner—Glenn K. Dawson
Assistant Examiner—Darwin P. Erezo
(74) Attorney, Agent, or Firm—Robert E. West

(57) ABSTRACT

A medicament respiratory delivery device including a housing having a chamber, an inlet and an outlet generally coaxially aligned with the chamber, wherein the chamber includes a medicament cartridge having a body including a generally cylindrical passage extending through the opposed ends of the cartridge generally coaxially aligned with the inlet and outlet of the housing, such that fluid delivered to the inlet ruptures the membranes, entrains medicament contained within the cartridge passage which is delivered to the patient's respiratory system through the outlet.

11 Claims, 10 Drawing Sheets

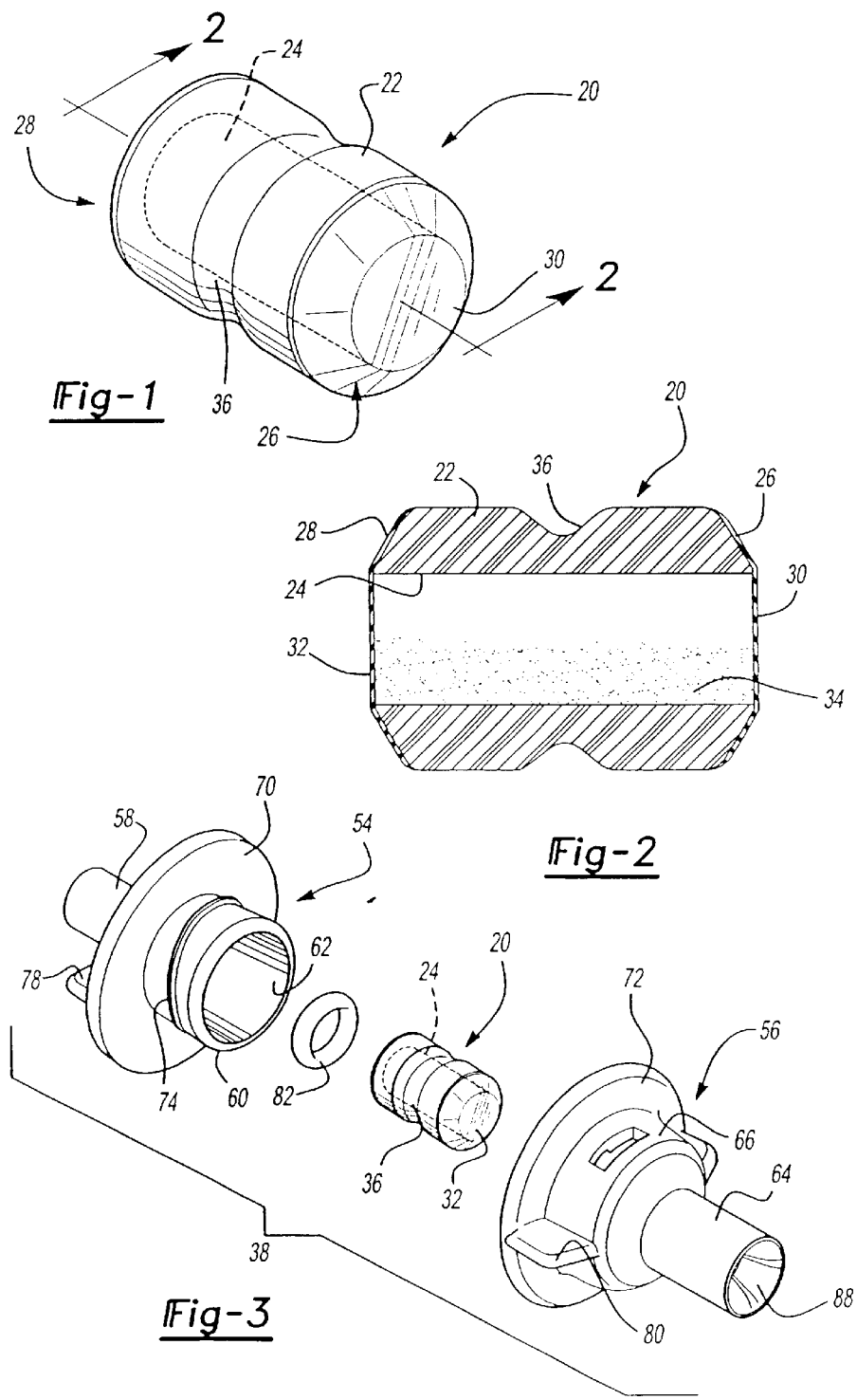

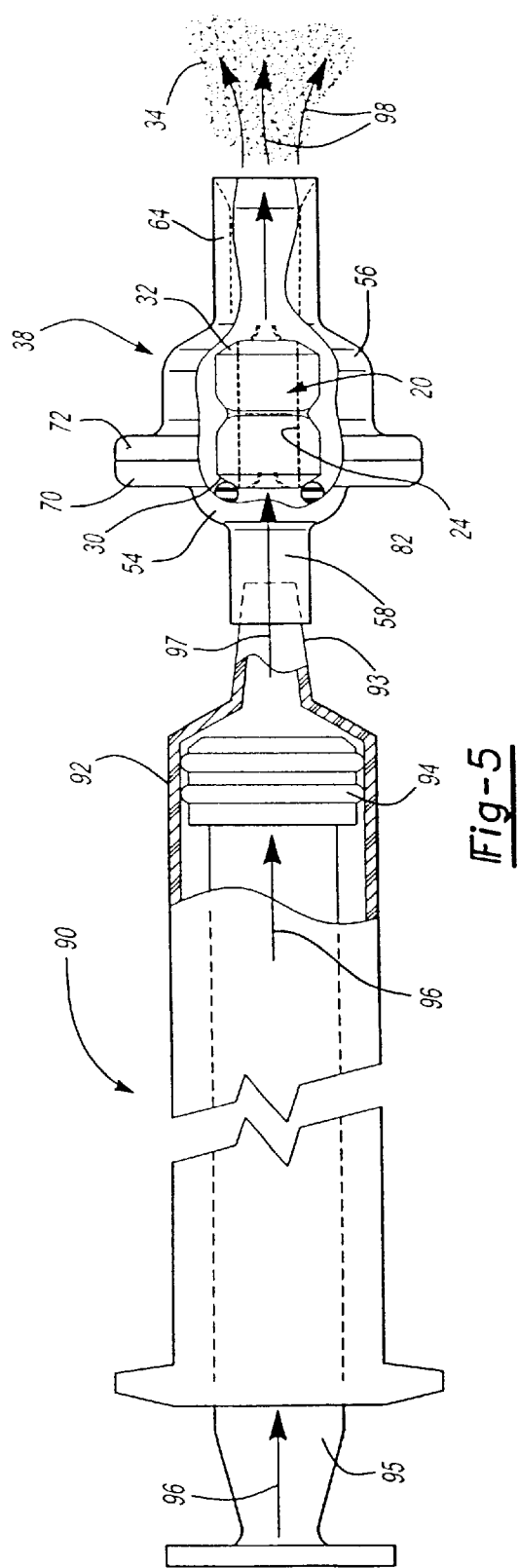

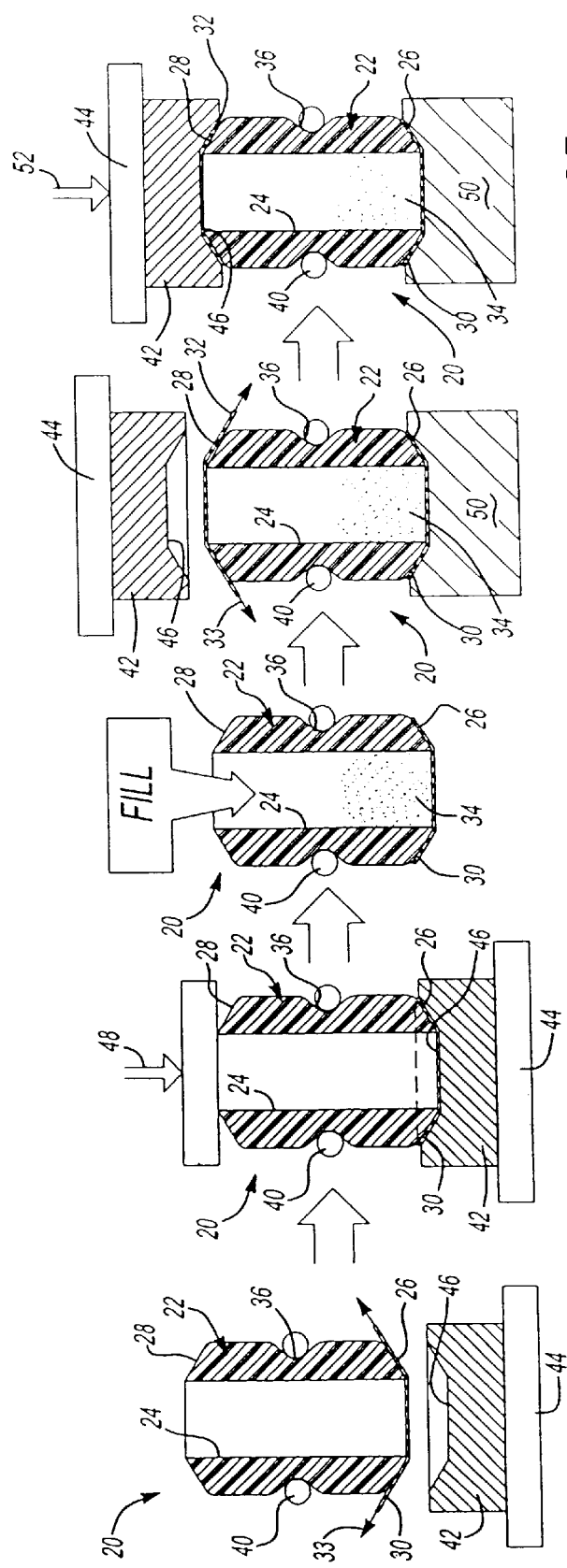

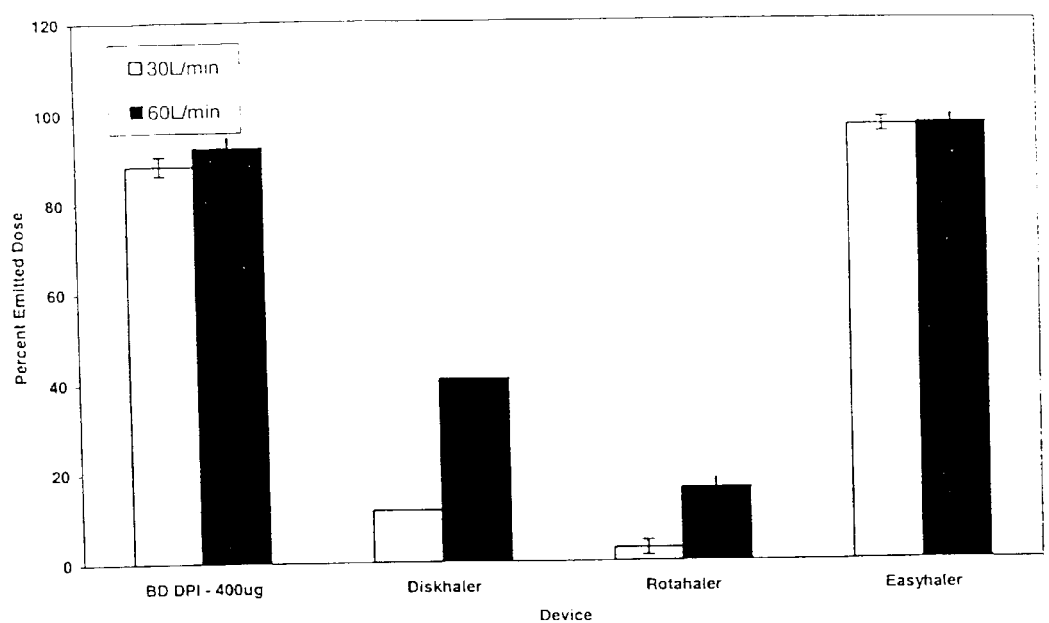
Figure 12. Emitted Dose at 30L/min and 60L/min

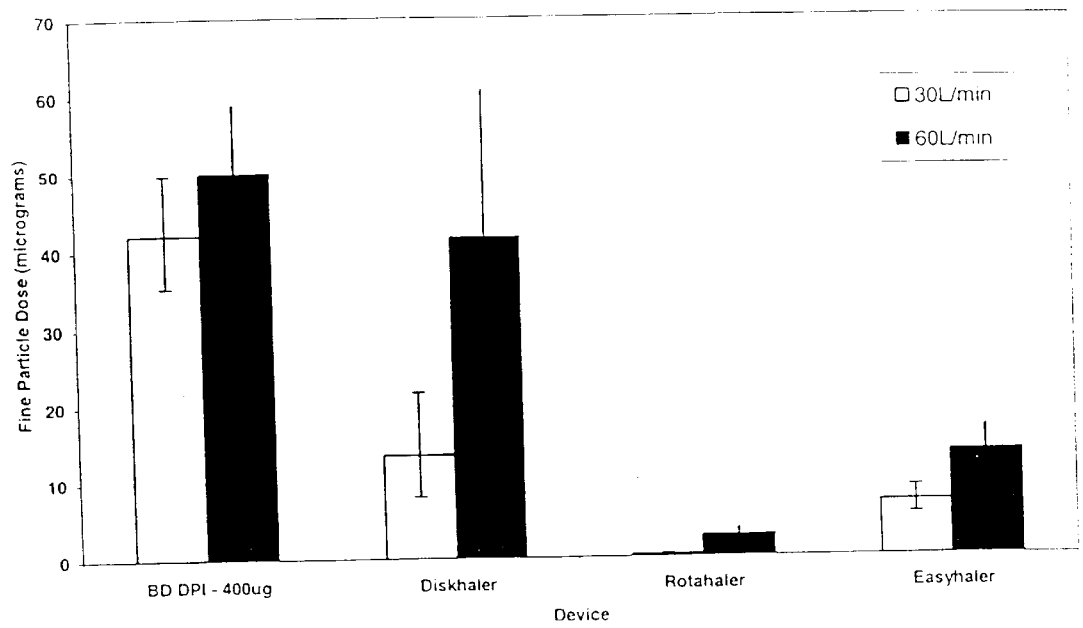
Figure 13 Fine Particle Dose at 30L/min and 60L/min

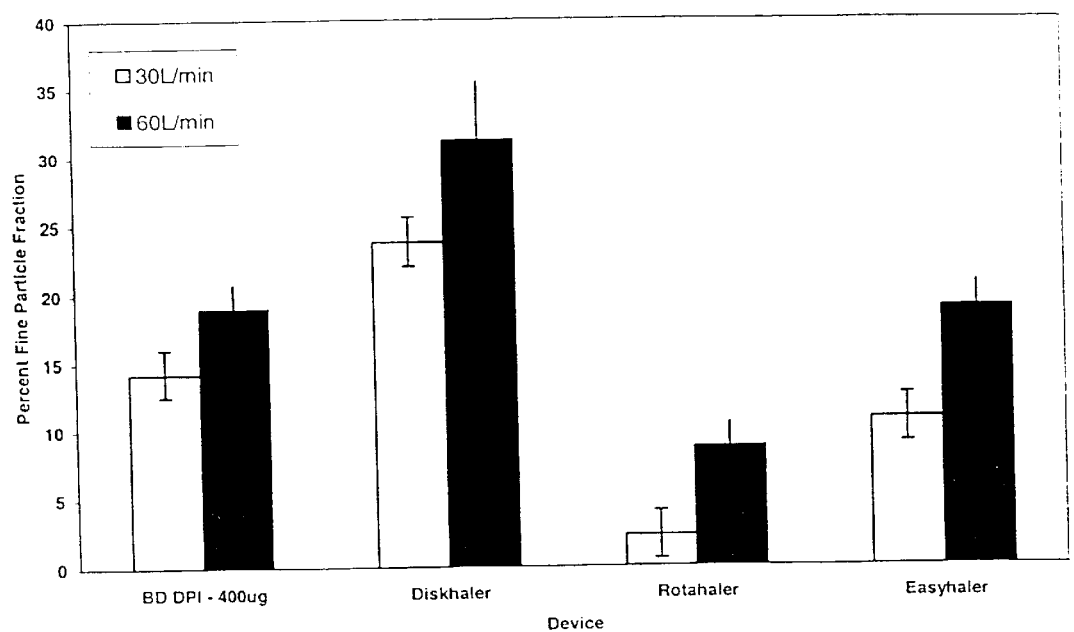
Figure 14 Fine Particle Fraction at 30L/min and 60L/min

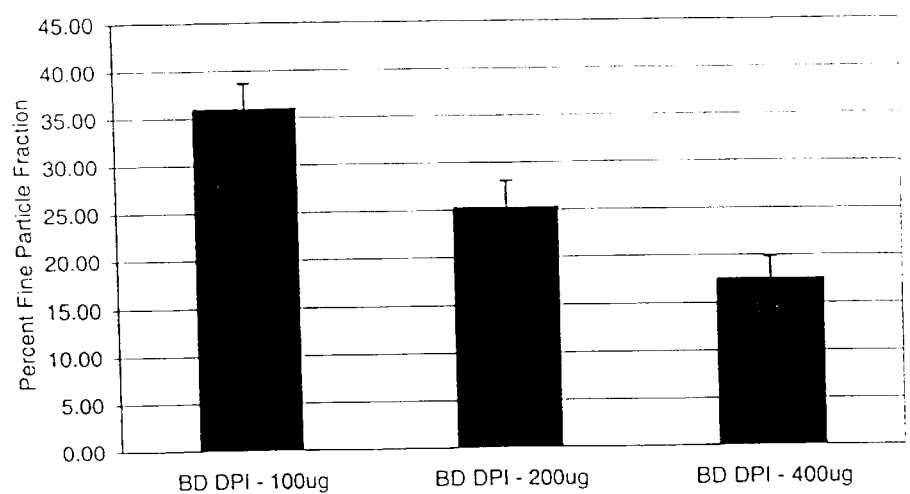
Figure 15 Fine Particle Fraction Results for Different Dose Levels at 60L/min

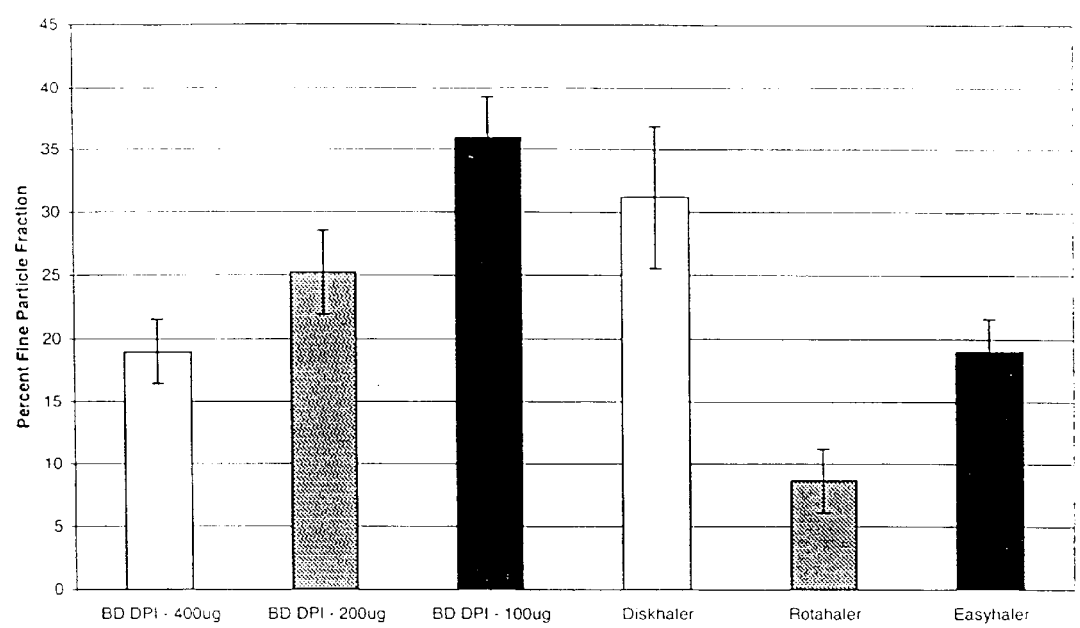
Figure 16 Fine Particle Fraction Results for Different Dose Levels at 60L/min for all devices.

MEDICAMENT RESPIRATORY DELIVERY DEVICE AND CARTRIDGE

RELATED APPLICATIONS

This Application is a continuation in part application of Ser. No. 09/879,517 filed Jun. 12, 2001, which is a continuation in part application of Ser. No. 09/758,776 filed Jan. 12, 2001.

FIELD OF THE INVENTION

This invention relates to medicament respiratory delivery devices including pulmonary, intranasal and buccal respiratory delivery devices having more efficient delivery of a medicament to the respiratory system of a patient.

BACKGROUND OF THE INVENTION

Inhalers and atomizers are now commonly used primarily to deliver various liquid medicaments via the patient's or user's nose or mouth. As used herein, "medicament" includes any powder or liquid medicament, drug or vaccine or combinations thereof which may be administered from an respiratory delivery device through the user's nose or mouth, sometimes referred to herein as a medicament respiratory delivery device. More recently, the prior art has proposed unit dose disposable powder medicament delivery devices, such as disclosed in U.S. Pat. No. 5,215,221, wherein a predetermined quantity or unit dose of a powder medicament is sealed in a reservoir formed between opposed thermoplastic sheets and expressed or delivered by application of manual force to a thermoformed blister which, upon activation, breaks a burstable seal between the sheets at the entrance to the reservoir and fluidizes the powder medicament in the reservoir through a delivery tube. The sealed delivery tube is cut prior to use.

There are several considerations affecting the design and efficacy of medicament respiratory delivery devices. First, it is important to ensure that a predetermined quantity or dose of medicament is consistently delivered to the user with each application. Second, because respiratory therapy often requires numerous applications, the cost of providing the dosage should also be considered. Thus, it is desirable that the medicament respiratory delivery device consistently express substantially all of the medicament to the user and that the delivery device is not susceptible to user error in operation. Third, it is important that the medicament be properly disbursed or entrained in the conveying fluid. Further considerations include the operating complexity, cost of the device, portability and size of the delivery device. It would also be desirable in certain applications to provide a reusable delivery device with a disposable standard medicament cartridge containing a unit dose of medicament which can be easily handled and replaced in the delivery device by the user without error. In other applications, a disposable delivery device is desirable.

The embodiments of the medicament respiratory delivery devices and medicament cartridge of this invention provide a reproduceable, high level of clearance of medicament or emitted dose from the cartridge upon manual actuation of the device with modest gas pressure as well as improved efficiency in the delivery of that medicament.

SUMMARY OF THE INVENTION

The cartridge for a medicament respiratory delivery device of this invention includes a body having opposed ends, a passage through the body and through the opposed ends, a medicament stored in the passage and burstable or pierceable membranes covering and sealing the passage at the opposed ends of the body. In the preferred embodiments, the opposed ends of the cartridge body surrounding the passage are convex and the burstable membranes are stretched taut over the convex opposed ends and bonded thereto, sealing the passage. In one disclosed embodiment, the opposed ends of the body are frustoconical surrounding the passage and the membranes comprise a thin polyolefin film heat-sealed or fused to the opposed frustoconical ends of the body. The term polyolefin is understood to mean a polymer containing olefin units such as, for example, ethylene, propylene or 1-butene units or any other alpha-olefin. Polyolefin as used herein includes polyethylene, polypropylene, ethylene- .alpha. olefin copolymer, wherein the alpha olefin having from 3 to 20, preferably 4 to 8 carbon atoms, polyolefin copolymers made by polymerizing olefins in the presence of a metallocene catalyst, ethylene-vinyl acetate copolymer, ethylene-ethyl acrylate copolymer, and ethylene-methyl acrylate copolymer. In particular, it is desirable to use polyethylene, such as low-density, linear-low-density, very-low-density, medium-density, or high-density polyethylene, or polypropylene, such as a polypropylene homopolymer, ethylene-propylene copolymer, or ethylene-propylene block copolymer.

In one preferred embodiment, the polymeric films which form the burstable membranes are preferentially oriented polyolefin films, preferably uniaxially oriented polyethylene films, angularly related, wherein the films oriented on the opposed ends of the cartridge are most preferably oriented at approximately right angles. It has been found by the applicant that burstable membranes formed of preferentially or uniaxially oriented polyolefin film, most preferably polyethylene film, wherein the films are oriented at approximately right angles, results in improved delivery of the medicament from the body passage or reservoir to the respiratory system of the user and results in a consistently greater emitted dose. Polyolefin films can be oriented by drawing in one or both mutually perpendicular directions in the plane of the film to impart strength thereto using methods known in the art. Oriented polyolefin films include machine direction and transverse direction orientation. Oriented polyolefin films include uniaxially or biaxially oriented films, with uniaxially films being preferred having a draw ratio of at least 1.2. Uniaxially-oriented films have properties to their advantage for use as the burstable membrane, including relatively high stiffness, as indicated by the tensile modulus in a particular direction, usually the machine direction, compared to the transverse direction. Properties of the oriented polyolefin film can be dependent to a certain degree on the particular process conditions under which the polyolefin film was manufactured. For example, a stiffer film with lower transverse burst pressure properties would result from an orientation process incorporating a larger machine direction orientation draw ratio. Thus, oriented polyolefins films can be tailored to provide an appropriate burst pressure property within a preferred film thickness range. Based upon computer modeling, consistently greater dosing is believed to result from turbulence or "turning" of the delivery fluid through the passage containing the medicament. Prototype testing indicates that the burstable membranes at the opposite ends of the cartridge in the delivery devices of this invention rupture nearly simultaneously using only a modest pressure. Where the membranes are preferentially or uniaxially oriented and perpendicular, the membranes each rupture in a slit near the center along the axis of the oriented films at approximately right angles to one another. This requires the fluid, such as a gas, to turn as the fluid is rapidly transmitted through the passage, entraining the medicament and expressing the entrained medicament through the slit formed in the second membrane. It has been found by the applicant that generally perpendicular orientation of the preferentially or uniaxially oriented films oriented at right angles resulted in an emitted dose of about 97%.

In another preferred embodiment, the burstable membranes are formed of a cast polyolefin copolymer of polyethylene and polyethylene methylacrylate copolymer film having a thickness of about 0.5 mil, wherein the films are stretched taut over the passage and heat sealed or fused to the opposed ends of the cartridge. Where the burstable membranes are formed of preferentially or uniaxially oriented polyethylene film, the film preferably has a thickness of about 1 mil. However, it is believed that the burstable membranes may also be formed of other polymers including, for example, polypropylene, acetate, polycarbonate, etc., wherein the film is preferably scored or embossed to reduce the required gas rupture pressure, thus having a rupture pressure of between 1.2 and 10 atmospheres, more preferably less than 5 atmospheres and most preferably between 1.5 and 4 atmospheres. Medicament cartridges employing such low burst pressure films allow for use of simple, manually actuated, pressurization mechanisms as described below. In one preferred embodiment of the cartridge for a medicament delivery device of this invention, the medicament passage or reservoir is generally cylindrical and the cartridge body is also generally cylindrical. An annular groove may be provided at the mid-portion of the body for ease of handling.

The methods of making a cartridge for a medicament respiratory delivery device of this invention includes forming a cartridge having first and second ends and a passage through the first and second ends of the cartridge; forming a thin polymeric film over the passage through the first end of the cartridge, sealing the passage through the first end; inserting a medicament into the passage through the second end of the cartridge; and applying a thin burstable polyolefin sheet over the second end of the cartridge having a burst pressure of less than 10 atmospheres, preferably less than 5 atmospheres, sealing the passage through the second end. In one preferred method of this invention, the method includes forming the cartridge from a polymer similar to the thin burstable polymeric sheet and bonding the polymeric sheet over the second end of the cartridge by heat bonding or fusing. Thus, a preferred method of forming the cartridge of this invention includes forming the cartridge from a polyolefin, preferably a polyethylene, and heat bonding a thin burstable polyolefin sheet to the second end of the cartridge by first stretching the film taut over the second end of the cartridge and then applying a heated die to the thin polyolefin film.

Based upon computer modeling, the highest medicament delivery rate is achieved using only one burstable polymeric membrane at the exit of the delivery device. This can be accomplished by removing the film sealing the first end of the cartridge prior to use, such as by piercing the membrane as disclosed in a copending application by the Applicant filed concurrently herewith. Where the cartridge includes burstable polymeric films over both ends of the cartridge, the most preferred embodiment of the method of this invention includes stretching taut polyolefin films over both ends of the cartridge prior to bonding the films to the opposed ends. In the most preferred embodiments, the cartridge is formed of a polymeric material having convex, preferably frustoconical, surfaces surrounding the passage and the film is stretched taut over the passage prior to bonding, thereby eliminating bowing or wrinkling of the film during heat sealing which may adversely affect the burst reproducibility, particularly where the fluid pressure is relatively low.

The embodiments of the medicament respiratory delivery device of this invention includes a housing having a chamber therein, an inlet port communicating with the chamber and an outlet port communicating with the chamber, preferably coaxially aligned with the inlet port. A cartridge is located within the housing chamber having opposed ends, a passage extending through the cartridge through the opposed ends, preferably generally coaxially aligned with the inlet and outlet ports of the housing, a medicament in the cartridge passage and burstable polymeric membranes covering the passage at the opposed ends of the cartridge. In one preferred embodiment of the medicament respiratory delivery device of this invention, the housing is formed of two releasably interconnected parts providing access to the chamber and replacement of the disposable cartridge. The gas inlet port includes an inlet tube communicating with the chamber for receipt of a collapsable fluid delivery device, such as a syringe barrel or compressible bulb. In one embodiment, the inlet tube includes a Luer connector adapted to receive a syringe barrel for supplying fluid or gas through the inlet tube to the cartridge.

In another preferred embodiment, the medicament respiratory delivery device is formed by thermoforming opposed polymeric sheets forming a chamber which encapsulates the medicament cartridge, inlet and outlet ports communicating with the chamber and a collapsible bulb at the inlet port which may comprise an integral thermoformed blister. In this embodiment, the body of the medicament cartridge preferably includes at least one and preferably two opposed integral flanges or wings, which are thermoformed between the sheets, assuring sealing of the chamber containing the cartridge. As described above, the burstable membrane at the outlet end of the cartridge preferably comprises a preferentially oriented polyolefin film, most preferably preferentially oriented polyethylene films at each end of the cartridge, wherein the films are oriented at approximately right angles, but may also comprise cast or embossed polyolefin films or other polymers.

The preferred embodiments of the medicament delivery device of this invention are particularly, but not exclusively, adapted for respiratory delivery including pulmonary, intranasal or buccal medicament delivery of a powder medicament, wherein the patient's inspiratory flowrate is not the driving force or pressure behind the aerosilization of the powder medicament. The powder is dispersed by fluid pressure that ruptures the membranes on the opposed ends of the cartridge, creating a substantially instantaneous fluid stream through the cartridge, entraining the powder particles into the fluid, which disperses the medicament to the respiratory system of the patient. This reduces the necessity for coordination of the patient's actuation of the device with the inspiratory flowrate and allows for less dependence of quantity of medicament delivered on patent's inspiration rate. As will be understood, however, the medicament respiratory delivery device of this invention, particularly including the cartridge, can also be utilized for liquid medicament delivery.

In preferred embodiments of the medicament respiratory delivery device and cartridge it has now been found that the efficiency of delivery of medicament is improved allowing for the use of reduced dosages of medicament while still achieving the same results as a higher dosage.

The method of delivering a medicament to the respiratory system of this invention includes providing a medicament respiratory delivery device including a cartridge having opposed inlet and outlet ends, a passage containing a medicament extending through the cartridge through the inlet and outlet ends, a thin burstable membrane, preferably a polyolefin membrane having a thickness of between 0.3 and 1.5 mils and having a burst pressure of between 1.2 and 10 atmospheres, preferably less than 5 atmospheres, sealing the passage at the outlet end of the cartridge and a manually compressible fluid delivery device communicating with the inlet end of the cartridge, such as a collapsible bulb or syringe as described above. The method then includes compressing the manually compressible fluid delivery device to deliver fluid to the inlet of the capsule, rupturing the burstable membrane, entraining the medicament in the fluid in an improved manner, dislodging fine particles of the active agent from carrier particled in the medicament and delivering increased amount of fine particles of the medicament to the respiratory system of the user.

In the preferred embodiments, the cartridge of the medicament respiratory delivery device includes a thin polyolefin burstable membrane having a burst pressure of less than 5 atmospheres sealing the passage at the inlet and outlet ends of the cartridge and the method then includes compressing the manually compressible fluid delivery device to deliver fluid to the burstable membrane at the inlet end of the cartridge, substantially simultaneously rupturing both burstable membranes, entraining the medicament in the fluid and delivering the medicament to the respiratory system of the user. In the most preferred embodiment, the passage at the inlet and outlet ends of the cartridge are sealed with preferentially oriented polyolefin films, wherein the orientation of the films are angularly related to each other and the method then includes delivering fluid to the inlet end of the cartridge, rupturing the film at the inlet end of the cartridge in a first slit, substantially simultaneously rupturing the burstable membrane at the outlet end in a second slit angularly related to the first slit, creating turbulence in the passage, entraining the medicament and expressing the medicament through the outlet end to the respiratory system of the user.

Other advantages and meritorious features of the medicament respiratory delivery device, medicament cartridge and method of making a cartridge for a medicament delivery device of this invention will be more filly understood from the following description of the preferred embodiments, the claims and the appended drawings, a brief description of which follows.

BRIEF DESCRIPTION OF THE DRAWINGS

FIG. 1 is an end perspective view of one preferred embodiment of the cartridge for a medicament respiratory delivery device of this invention;

FIG. 2 is a side cross-sectional view of the cartridge shown in FIG. 1, in the direction of view arrows 2—2;

FIG. 3 is an exploded view of one preferred embodiment of the medicament respiratory delivery device and cartridge of this invention;

FIG. 5 is a side partially cross-sectioned view of the medicament delivery device shown in FIGS. 3 and 4 attached to a conventional syringe barrel during delivery of the medicament contained in the cartridge;

FIG. 8 is a sequence drawing illustrating the method of forming and filling the cartridge illustrated in FIGS. 1 and 2, above;

FIG. 12 is a graph comparing the results of flow rate of various medicament respiratory delivery devices on emitted dose;

FIG. 13 is a graph comparing flow rate of various medicament respiratory delivery devices on fine particle dose;

FIG. 14 is a graph comparing flow rate of various medicament respiratory delivery devices on fine particle fraction;

FIG. 15 is a graph comparing fine particle fraction and emitted dose level of one preferred embodiment of a medicament respiratory delivery device at a constant flow rate; and FIG. 16 is a graph comparing fine particle fraction and emitted dose level of various medicament respiratory delivery devices at a constant flow rate.

DESCRIPTION OF THE PREFERRED EMBODIMENTS

Figure 4:
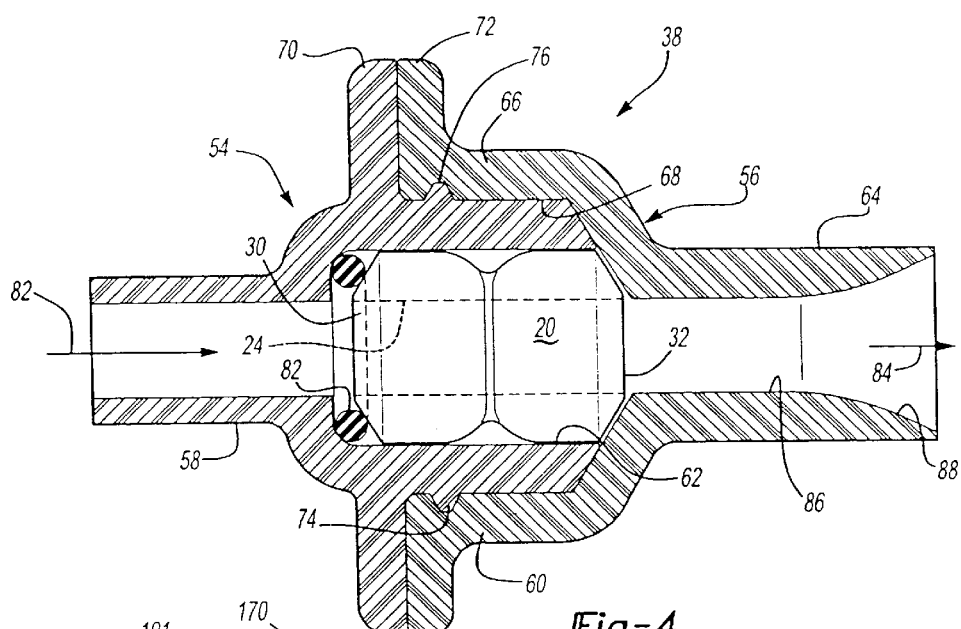
FIG. 4 is a side cross-sectional view of the assembled medicament respiratory delivery device shown in FIG. 3.

The medicament respiratory delivery device, cartridge, method for forming a cartridge for a medicament delivery device and method of delivering a medicament to the respiratory system will now be described with reference to the accompanying drawings, in which preferred embodiments of the inventions are shown. However, as will be understood by those skilled in this art, the drawings are intended to be merely illustrative of preferred embodiments, and this invention should not be construed as limited to the embodiments disclosed in the drawings, wherein like numbers refer to like elements throughout.

The cartridge for a medicament respiratory delivery device 20 shown in FIGS. 1 and 2 includes a body 22 having a passage extending through the body 22 through the opposed ends 26 and 28. The passage is sealed at the opposed ends 26 and 28 of the body by polymeric films or membranes preferably polyolefin films 30 and 32, respectively, having a burst pressure of less than 10 atmospheres, most preferably less than 5 atmospheres. As will be understood from the following description of the preferred embodiments, the method of delivering a medicament to the respiratory system and medicament respiratory delivery device of this invention delivers the medicament at a relatively modest pressure to the respiratory system as compared to other devices requiring a greater pressure, such as intradermal devices. In the most preferred embodiments of the medicament respiratory delivery device, fluid pressure is delivered to the inlet of the cartridge by a manually compressible fluid delivery device, such as a syringe or collapsible bulb, wherein burst pressure of the burstable membranes is between 1.2 and 10 atmospheres or more preferably less than 5 atmospheres and most preferably between 1.5 and 4 atmospheres. The passage 24 through the body serves as a vessel or reservoir containing a suitable medicament 34. As set forth above, and described further below, the medicament 34 may be any medicament, drug or vaccine or combinations thereof used to deliver, via the nasal, pulmonary or buccal routes used in the prevention, alleviation, treatment or cure of diseases. Examples of such medicaments are set forth below. In the disclosed embodiment, the passage 24 includes a unit dose of a powder medicament 34. However, the passage 24 may alternatively include a liquid medicament. In addition, it has now been shown possible to include lesser amounts of the powder medicament to achieve the same effects of a larger dose in other, commercial devices.

As shown in FIGS. 1 and 2, the body 22 of the cartridge is generally cylindrical having an intermediate or central V-shaped groove for ease of handling and, where the cartridge is replaceable, the body portions on opposed sides of the central groove 36 are preferably symmetrical such that the cartridge 20 may be loaded into the medicament delivery device 38 described below in either orientation, avoiding mistakes by the user. The passage 24 is preferably cylindrical, but may also be hourglass-shaped or other shapes depending upon the medicament, actuation means, etc. As described below with regard to the preferred method of making the cartridge 20 shown in FIG. 8, the body 22 is preferably formed of a thermoplastic and preferably is the same as or chemically similar to the polymer used for the membranes 30 and 32 which, in the most preferred embodiment, are formed of polyolefin, most preferably polyethylene or a polyolefin blend or copolymer.

FIG. 8 illustrates a preferred method of making and filling the medicament cartridge 20 illustrated in FIGS. 1 and 2. As set forth above, the body 22 of the cartridge is preferably formed from a polymer which is compatible with or chemically similar to the burstable membranes to permit heat bonding or fusing of the membranes to the end surfaces 26 and 28 of the cartridge. Thus, the body 22 may be formed of a polyolefin, preferably polyethylene, a polyethylene blend, copolymer or other suitable polymers by injection molding or other known molding processes. The body 22 has a generally cylindrical passage 24 extending through the ends 26 and 28 of the body and a radial groove 36 at the midportion of the body for ease of handling. As shown in FIG. 8A, the first membrane 30 is preferably stretched taut over the first end 26 of the body as shown by arrows 31. The body may be supported in a ring 40 or other suitable fixture opposite a heated die 42 which is supported on a platen 44. In the preferred embodiment, the opposed ends 26 and 28 of the body 22 are convex or beveled outwardly to assure that the membranes are stretched taut over the ends of the passage 24 as shown in FIG. 8A. In the preferred embodiment, the membranes are stretched taut over a convex surface to avoid wrinkles in the membrane covering the passage which may affect the consistency or reproducibility of the burst pressure of the membranes which, as described below, preferably substantially simultaneously rupture as fluid is delivered under pressure to the passage. It is not necessary or desirable to stretch the membrane as it is stretched taut over the passage which may also affect the burst pressure or force. In the most preferred embodiment, the end surfaces 26 and 28 are frustoconical surrounding the passage 24 before fusing as shown. The heated die 42 includes a concave surface 46 which compliments the frusto-conical surface 26.

The heated die 42 is then brought into contact with the taut membrane as shown in FIG. 8D by arrow 48, heat bonding or fusing the polymeric membrane 30 to the convex end surface 26 of the body as shown by arrow 48. As set forth above, this method avoids bowing or wrinkling of the thin polymeric membrane 30, thereby assuring reliable functioning of the membrane and simultaneous bursting of the membranes as described further below. The cartridge may then be filled with a suitable medicament, such as the powder medicament 34 as shown in FIG. 8C, through the passage 24 through the second end 28 of the body 22. As set forth above, the cartridge 20 is preferably filled with a unit dose of a medicament for use in a suitable medicament respiratory delivery device, such as the devices described below.

The second membrane 32 is then applied over the second end 28 of the body 22 using the same heated die 42 or a second heated die as shown in FIGS. 8D and 8E. That is, the first end is supported on a die member 50 and the second polymeric membrane 32 is stretched taut over the passage 24 of the body 22 as shown by arrows 33 opposite the heated die 42 as shown in FIG. 8D. The heated die 42 is then brought into contact with the stretched polymeric membrane 32 as shown in FIG. 8E by arrow 52, thereby heat bonding or fusing the polymeric membrane 32 to the second end 28 of the body 22 as shown by arrow 52 in FIG. 8E. As described above, the preferred burstable membranes 30 and 32 are formed of polyolefin, most preferably polyethylene, a polyethylene blend or copolymer having a thickness of between 0.3 and 1.5 mils. Having a burst pressure of less than 10 atmospheres or more preferably less than 5 atmospheres and most preferably between 1.5 and 4 atmospheres Thus, the body 22 is also preferably formed of polyethylene, a polyethylene blend or copolymer. In the most preferred embodiment, the membranes 30 and 32 are formed of preferentially or a uniaxially oriented polyethylene, wherein the first membrane 30 is oriented generally perpendicular to the axial orientation of the second membrane 32.

Various modifications may be made to the disclosed method of forming and filling the cartridge 20 shown in FIG. 8. As set forth above, computer modeling and prototype testing of the fluid dynamics of the dispersion of powder medicament indicates that the most preferred embodiment of the cartridge 20 includes a thin polyolefin burstable membrane, preferably an oriented polyolefin film, only at the outlet of the cartridge, contrary to the teaching of the prior art. Thus, it would be possible to utilize only one polyolefin burstable membrane having a burst pressure preferably less than 10 atmospheres or more preferably less than 5 atmospheres and provide an alternative closure at the opposed end which, for example, could be pierced or otherwise removed prior to actuation of the manually compressible delivery device. The method would then include sealing one end of the cartridge preferably with a suitable film or sheet, filling the cartridge as shown in FIG. 8, and sealing the opposed end preferably with a thin polyolefin burstable membrane, following the same steps shown in FIG. 8 except that one end of the passage 24 is closed by any suitable method with a film or sheet including injection molding. The first end could, for example, be sealed during the molding process.

As will be understood, the medicament cartridge of this invention may be utilized with various medicament respiratory delivery devices preferably having a manually compressible fluid delivery device including, but not limited to the embodiments of the medicament respiratory delivery devices shown and described below. The housing of one embodiment of a medicament respiratory delivery device 38 shown in FIGS. 3 and 4 is comprised of two releasably interconnected components, namely an inlet housing member 54 and an outlet housing member 56. The inlet housing member 54 includes a fluid inlet tube 58 and an enlarged tubular portion 60 defining a generally cylindrical chamber or passage 62 which is coaxially aligned with the inlet tube 58 and the passage 24 through the cartridge 20 when the cartridge is assembled in the housing members as shown in FIG. 4. The outlet housing member 56 includes a fluid outlet tube 64 and a bell-shaped tubular portion 66 having an opening 68 which receives the enlarged tubular portion 60 of the inlet housing member 54 as shown in FIG. 4. The disclosed embodiment of the inlet and outlet housing members 54 and 56 include mating flange portions 70 and 72, respectively. In this embodiment, the enlarged tubular portion 60 includes a male thread 74 and the internal surface 68 of the bell-shaped portion 66 includes an internal thread 76, as shown in FIG. 4, such that the housing components may be easily threaded together following receipt of the medicament cartridge 20 in the passage 62 of the inlet housing member 54 as shown in FIG. 4. Radial gripping flanges 78 and 80 may be provided on the inlet housing member 54 and outlet housing member 56 as shown in FIG. 3 to assist in threaded assembly of these members. A resilient elastomeric O-ring 82 is provided in the chamber 62 of the inlet housing member 54 to assure sealed relation between the cartridge 20 and the chamber 62 as best shown in FIG. 4, taking up any tolerance variations between the cartridge 20 and the cylindrical chamber or passage 62. The medicament respiratory delivery device 38 is then assembled by inserting the medicament cartridge 20 described above in the cylindrical passage 62 of the inlet housing member 54, which preferably includes an O-ring 82, then threading the bell-shaped portion 66 of the outlet housing member 56 on the enlarged tubular portion 60, releasably retaining the inlet and outlet housing members as shown in FIG. 4.

As will be understood, the medicament respiratory delivery device 38 may be utilized with various manually compressible pressure actuation or delivery devices which introduce gas, liquid or other fluids under a moderate pressure of preferably less than 10 atmospheres through the inlet tube 58 as shown by arrow 82, thereby rupturing the burstable membranes 30 and 32, entraining the medicament in the passage 24 and delivering the medicament in a plume through the outlet tube 64 as shown by arrow 84. Where the medicament is to be delivered to the patient through the mouth or nose of the patient, for example, the passage 86 through the outlet tube 64 preferably includes a generally cone-shaped arcuate passage 88 at the outlet which further expands, spreads and slows the outlet plume for improved dispersion of the powder medicament.

The preferred fluid delivery device for the disclosed embodiments of the medicament respiratory delivery device 38 (and 138 described below) is a conventional syringe 90 shown in FIG. 5. The syringe 90 shown in FIG. 5 includes a syringe barrel 92 having a reduced diameter tubular tip portion 93 which is slightly tapered to be press fit into the tubular portion 58 of the inlet housing member forming a "Luer Fit" as shown in FIG. 5. The syringe 90 includes a stopper 94, generally formed of an elastomeric material, in sealed reciprocal relation, which is connected by conventional means to a plunger 95. The syringe barrel 92 may contain a gas, such as air, or may alternatively contain a liquid diluent or medicament. Actuation of the medicament respiratory delivery device 38 is accomplished by moving the plunger 95 into the barrel portion 92 as shown by arrows 96, which drives the stopper 94 through the barrel portion 92 creating a build-up of fluid pressure in the chamber formed between the stopper 94 and the burstable membrane 30 at the inlet port as shown by arrow 97. When the pressure reaches the burst force at the membranes 30 and 32, the membranes rupture substantially simultaneously as described above.

The fluid rapidly traveling through the passage 24 of the cartridge 20, entrains the medicament 34 contained in the passage, and propels the entrained medicament in an expanding plume through the outlet tube 64 as shown by arrows 98. Where the medicament is taken through the mouth, the outlet tube 64 serves as a mouthpiece. Alternatively, as described above, an outlet tube 64 for delivery to the patient's nose may be used.

Figure 6:
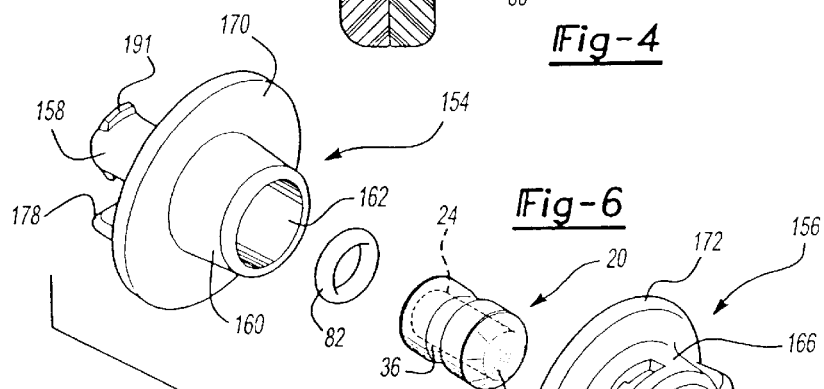
FIG. 6 is an exploded view of an alternative embodiment of the medicament respiratory delivery device of this invention.

FIG. 6 illustrates an alternative embodiment of a medicament respiratory delivery device 138 which is very similar to the medicament respiratory delivery device 38 described above and therefore has been numbered in the same sequence. The medicament delivery device 138 shown in FIG. 6 includes two housing members, including an inlet housing member 154 and an outlet housing member 156. The inlet housing member 154 includes an inlet tube 158 having a Luer threaded connector 191 and an enlarged generally tubular portion 160 having a generally cylindrical chamber 162. The inlet and outlet housing members including mating radial flange portions 170 and 172, respectively. In this embodiment, however, the external surface of the enlarged generally tubular portion 160 of the inlet member 154 is conical and press-fit in the generally cylindrical opening (not shown) in the bell-shaped tubular portion 166, eliminating the requirement for male and female threads 74 and 76 shown in FIGS. 3 and 4. Further, the threaded Luer connector is adapted to be threaded to a syringe having a conventional threaded Luer connector (not shown). Otherwise, the medicament respiratory delivery device 138 shown in FIG. 6 may be otherwise identical to the delivery device 38 described above and therefore no further description is required. As will be understood, the medicament respiratory delivery device 138 shown in FIG. 6 is assembled as described above by first inserting the medicament cartridge 20 in the generally cylindrical chamber 162 of the inlet housing member 154, preferably with an O-ring 82 as described above. The enlarged tubular portion 160 having a conical exterior surface is then press fit into the cylindrical opening in the bell-shaped portion 166 and the medicament delivery device 138 is then ready for use.

Figure 7:
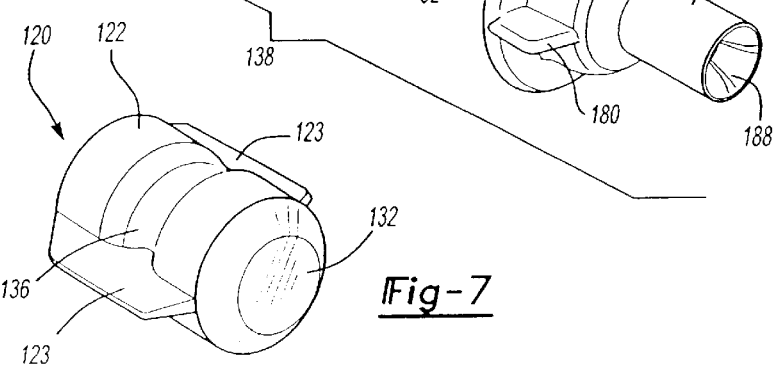
FIG. 7 is an alternative embodiment of the medicament cartridge of this invention.

The embodiment of the medicament cartridge 120 shown in FIG. 7 is very similar to the medicament cartridge 20 shown in FIGS. 1 and 2 except that the body 122 is formed with radially extending integral flange portions 123, which may be injection molded with the body 122. The burstable membranes (one of which is shown at 132) on the opposed ends of the body 122 are affixed to the end portions as described above. Otherwise, the cartridge 120 may be identical to the cartridge 20 described above and numbered in the same sequence and the components are numbered in the same sequence such that no further disclosure is required.

Figure 9:
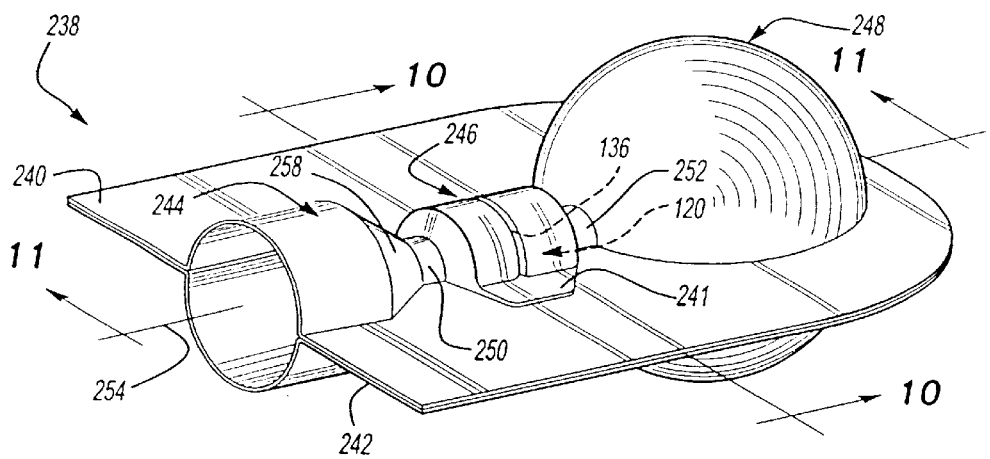
FIG. 9 is a top perspective view of an alternative embodiment of the medicament respiratory delivery device of this invention.
Figure 10:
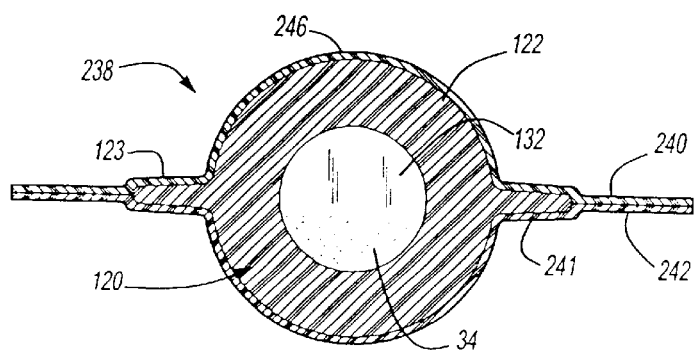
FIG. 10 is an end cross sectional view of FIG. 9 in the direction of view arrows 9—9.
Figure 11:
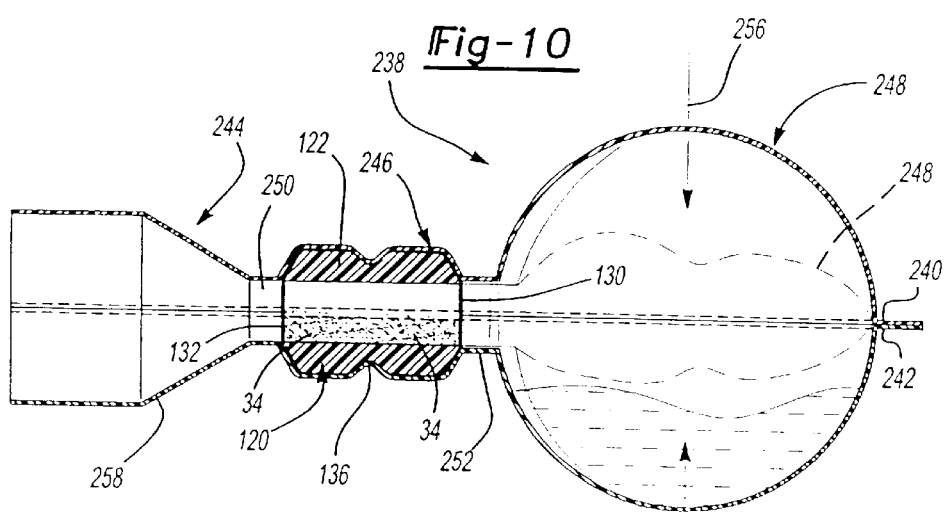
FIG. 11 is a side cross sectional view of FIG. 9 in the direction of view arrows 11—11.

The embodiment of the medicament respiratory delivery device shown in FIGS. 9 to 11 is formed by thermoforming two thermoplastic sheets 240 and 242 by conventional methods including vacuum forming, wherein the thermoformed polymeric sheets are formed and fused together and encapsulate the medicament cartridge 120. In the preferred embodiment of the medicament respiratory delivery device 238, the medicament cartridge 120 is formed as shown in FIG. 7, wherein the body 122 includes integral radially and axially extending flanges 123. The integral flanges 123 assure sealing of the thermoformed chamber portion 246 which receives the cartridge or cartridge 120, wherein the thermoformed sheets 240 and 242 are bonded to the flange portions 123 as shown at 241. This also prevents rotation of the cartridge 120 in the vacuum formed delivery device.

As best shown in FIGS. 9 and 11, the thermoformed medicament respiratory delivery device 238 includes an outlet portion 244, a chamber portion 246 and a compressible delivery device 248 in the form of an integral bulb or blister which, in the disclosed preferred embodiment, is generally spherical and symmetrical about the longitudinal axis 254. As will be understood, however, the compressible delivery device may take various forms, including a bellows-type pressure actuator (not shown) either symmetrically formed about the axis 254 or extending from only one of the sheets 240 or 242. A separate pressure actuator, such as a separate bulb, may also be utilized. The thermoformed medicament delivery device 238 also includes a generally tubular outlet portion 250 and a generally tubular inlet portion 252. The medicament respiratory delivery device 238 shown in FIGS. 9 to 11 is disposable because of the very low cost to manufacture compared to the medicament respiratory delivery devices 38, 138 shown in FIGS. 3 to 6 described above. However, the medicament respiratory delivery devices 38 and 138 described above have the advantage that the delivery device is reusable by replacing the cartridge.

The medicament respiratory delivery device 238 is operated by the user by compressing the bulb 248 as shown by arrows 256, which delivers fluid under pressure through the tubular inlet portion 252 to the first burstable membrane 130. However, as described above, the burstable membranes 130 and 132 rupture substantially simultaneously, entraining the medicament 34 contained in the cartridge 246, delivering a plume of medicament entrained in the gas through the tubular exit portion 250 into the exit diffuser 258. In the most preferred embodiment, the burstable films 130 and 132 are preferentially oriented, most preferably uniaxially oriented polyolefin or more preferably oriented polyethylene films, wherein the films are oriented at approximately right angles. As set forth above, the applicant has discovered that preferentially or uniaxially polyethylene film having a thickness of about 1.0 mil and a burst pressure of between 1.2 and 10 atmospheres, more preferably less than 5 atmospheres or most preferably between 1.5 and 4 atmospheres provides a higher emitted dose in a medicament respiratory delivery device of the type described herein using other burstable films.

Prototype testing indicated that perpendicular uniaxially oriented polyethylene films having a thickness of about 1 mil having a burst pressure of about 3 atmospheres resulted in an emitted dose of about 97% of a powder medicament having a particle size of 1 to 5 microns. Burst tests of burstable membranes were conducted by the applicant using a syringe as shown in FIG. 5 at 90 to deliver gas under pressure to a cartridge in a test fixture simulating the medicament respiratory delivery devices of this invention. The cartridge was formed as described herein having a surface area of 0.049 $in^2$ (3 mm diameter) covering the passage. The stopper 94 was moved through the barrel 92 under controlled conditions at 25 in/min and the burst pressure (force divided by area) and emitted dose (i.e. percentage of powder emitted from the passage, HPLC assay) was measured. 1 to 5 microns is preferred for pulmonary delivery of powder medicament, such as insulin. The preferred particle size for intranasal delivery is 50 to 100 microns. The applicant also tested other burstable films or membranes with the following results. A cast 50/50 copolymer of ethylene and methylacrylate having a thickness of 0.5 mil and burst pressure of about 2 atmospheres resulted in an emitted dose of about 95%. As used herein, "polyolefin" includes polymers derived from simple olefins including polyethylene, polypropylene, polybutenes, etc., copolymers and blends. As used herein, "polyethylene," includes polyethylene blends and copolymers with and without additives. Uniaxially oriented polyethylene films having a thickness of about 0.5 mil having a burst pressure of about 3 atmospheres, wherein the films were oriented approximately parallel, resulted in a 93% emitted dose rate. The applicant also tested a polyethylene film having a thickness of bout 0.9 mil wherein the polyethylene film had a checker board embossment having a burst pressure of about 3 atmospheres, wherein the emitted dose rate was about 91%. Thus, the preferred embodiments of the cartridge for a medicament respiratory delivery device of this invention include burstable membranes formed of polyethylene film having a thickness of between about 0.3 mil to about 1.5 mil, wherein the preferred range is between 0.5 and one mil and a burst pressure of between 1.2 and 10 atmospheres or more preferably less than 5 atmospheres and most preferably between 1.5 and 4 atmospheres. It is believed, however, that films formed of other polymers may be used including, for example, polypropylene, acetate and polycarbonate; however, it is also believed that such other films should be scored or embossed to reduce the burst pressure.

EXAMPLE

Experiments were preformed to compare the performance of the respiratory medicament delivery device and cartridge of FIGS. 9–11 to currently marketed devices at various flow rates. The currently marketed products chosen were the Orion Pharma Buventol Easyhaler® inhalation device, Glaxo Wellcome Rotahaler® inhalation device with Ventoline Rotacaps®, and the Glaxo Wellcome Ventolin Diskhaler inhalation device, which are used for the prevention and relief of bronchospasms in patients with reversible obstructed airway disease. All of these devices consist of micronized albuterol sulfate blended with less finely milled lactose carrier particles, as known in the art. Together the medicament and lactose particle form agglomerates. When these devices are activated the lactose carrier particles are separated and agglomerates are broken up.

Preferred embodiments of cartridges disclosed herein were loaded with a blend prepared by jet-milling albuterol sulfate to a mean particle size of 1.21 $\mu$m and then blended with lactose particles having a mean particle size of 60 $\mu$m.

The devices were then activated at both 30 and 60 L/minute flow rates. the emitted dose and particle size of the dry powders were analyzed using an Anderson Cascade Impactor.

As can be seen in the graph of FIG. 19, at both 30 and 60 L/minute flow rates, it was found that the emitted dose for the preferred medicament respiratory delivery device and cartridge (hereinafter "$DPI_4$") was significantly higher than for the Rotahaler® inhalation device. A distinct interaction was found in the currently marketed medicament respiratory delivery device between emitted dose and flow rate. $DPI_4$ showed little flow rate dependence.

As shown in FIG. 20 $DPI_4$ showed and average fine particle dose (hereinafter "FPD") equal to 50.1 mg at a flow rate of 60 L/minute. FPD is defined as the sum of albuterol with aerodynamic diameter less than 4.5 mm divided by the number of doses discharged from the device. Statistically, $DPI_4$ had a higher FPD than the Rotahaler® and the Easyhaler® devices. In addition, there was little change in FPD, for $DPI_4$, when the flow rate was varied from 30 to 60 L/minute flow rates.

The fine particle fraction (hereinafter "FPF") of $DPI_4$ was found to be 19%, see the graph of FIG. 21, and was not statistically different than the Easyhaler® (19%) and the Rotahaler® (8.7%) devices. $DPI_4$ had a lower FPF than the Diskhaler® device (31.2%) but this is believed to be explained by the inverse relationship, in the Diskhaler® device, between emitted dose and FPF, where a low dose contributed to a higher value for FPF.

It was also found, see the graph of FIG. 22, that the FPF for $DPI_4$ depends on dose loading. Generally, for $DPL_4$, as the dose decreases, the FPF increases. This demonstrates the efficiency of $DPI_4$ where a smaller amount of active can achieve a greater FPF, thus allowing less blend to be used to achieve the same efficacy as the other devices tested. The dose level outlined in FIGS. 19–22 for DPL was that giving the lowest FPF and FPD results (i.e., 400 μg/dose).

Comparison of the other devices with for $DPI_4$ at 100 μg/dose or 200 μg/dose levels would be even more favorable for $DPI_4$, see FIG. 23. This shows that smaller amount of blend can be loaded into the preferred medicament respiratory delivery device and cartridge and still deliver a greater portion of the active to the fine particle portion of the lungs.

Preferred embodiments of the medicament respiratory delivery devices disclosed herein preferably generate an emitted dose of medicament with a fine particle fraction of at least 18.5% albuterol sulfate.

Where the manually compressible fluid delivery device or pressure actuator is a collapsible or compressible bulb or some other pressure actuation device having fluid such as air or liquid in the and an outlet in communication with the inlet end of the cartridge, the method of delivering a medicament to the respiratory system includes activating the pressure actuator to deliver fluid under pressure to the inlet of the cartridge, rupturing the burstable membrane, entraining the medicament contained therein, dislodging fine particles of the medicament and delivering the entrained fine particles of medicament to the respiratory system of the patient.

As will be understood, the medicament respiratory delivery device and cartridge of this invention may be utilized to deliver various substances including medicaments, drugs and vaccines or combinations thereof to the respiratory system via the nasal, pulmonary or buccal routes used in the prevention, diagnosis, alleviation, treatment or cure of diseases. These substances may include, for example, (i) drugs such as Anti-Angiogenesis agents, Antisense, anti-ulcer, butorphanol, Calcitonin and analogs, COX-II inhibitors, desmopressin and analogs, dihydroergotamine, Dopamine agonists and antagonists, Enkephalins and other opioid peptides, Growth hormone and analogs (including growth hormone releasing hormone), Growth hormone antagonists, IgE suppressors, Insulin, insulinotropin and analogs, Ketamine, Kytril, Leutenizing hormone releasing hormone and analogs, lidocaine, metoclopramide, Midazolam, Narcotic analgesics, neuraminidase inhibitors, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, vasopressin; (ii) vaccines with or without carriers/adjuvants such as prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, arthritis, cholera, cocaine addiction, HIB, meningococcus, measles, mumps, rubella, varicella, yellow fever, Respiratory syncytial virus, pneumococcus, streptococcus, typhoid, influenza, hepatitis, including hepatitis A, B, C and E, polio, HIV, parainfluenza, rotavirus, CMV, chlamydia, nontypeable haemophilus, moraxella catarrhalis, human papilloma virus, tuberculosis including BCG, gonorrhoea, asthma, atheroschlerosis, malaria, otitis media, *E-coli*, Alzheimers, H. Pylori, salmonella, diabetes, cancer and herpes simplex; and (iii) other substances in all of the major therapeutics such as Agents for the common cold, Anti-addiction, anti-infectives, analgesics, anesthetics, anorexics, antiarthritics, anti-allergy agents, antiasthmatic agents, anticonvulsants, anti-depressants, antidiabetic agents, antidepressants, anti-diuretics, anti-emetics, antihistamines, anti-inflammatory agents, antimigraine preparations, antimotion sickness preparations, antinauseants, antineoplastics, anti-obesity, antiosteoporeteic, antiparkinsonism drugs, antipruritics, antipsychotics, antipyretics, antitussiers, anticholinergics, benzodiazepine antagonists, bone stimulating agents, bronchial dilapors, central nervous system stimulants, corticosteroids, hormones, hypnotics, immunosuppressives, mucolytics, prostaglandins, proteins, peptides, polypeptides and other macromolecules, psychostimulants, rhinitis treatment, sedatives, sexual hypofunction, tranquilizers and vitamins including B12.

Having described preferred embodiments of the medicament cartridge, method of forming same, medicament respiratory delivery device and method of delivering medicament to the respiratory system of this invention, it will be understood that various modifications may be made within the purview of the appended claims. For example, as set forth above, the cartridge may include only one polymeric burstable membrane, wherein the passage through the opposed end may be sealed by a pierceable film or a film which is removed or pierced prior to use. In such embodiments, the burstable polymeric film is preferably located at the exit end of the passage which prototype testing has established results in an excellent distribution of the medicament contained in the cartridge. Further, the passage through the cartridge is preferably generally cylindrical; however, the passage may also include other configurations including for example an hourglass shape. Further, although the medicament respiratory delivery device of this invention was developed for delivery of a powder medicament, the cartridge of this invention is suitable for delivery of a liquid or gaseous medicament or the syringe or bulb may include a liquid medicament or dilvent and the cartridge may include a powder medicament. As set forth above, the medicament cartridge of this invention may also be utilized with various medicament respiratory devices and is not limited to the medicament delivery devices disclosed herein.

What is claimed is:

1. A medicament respiratory delivery device, comprising:
 a housing comprised of two opposed thermoformed bonded thermoplastic sheets, said sheets having formed therebetween a chamber, an inlet communicating with said chamber, a pressure actuator having an outlet communicating with said inlet of said chamber and an outlet communicating with said chamber opposite said inlet of said chamber; and
 a medicament cartridge in said chamber encapsulated by said sheets, said medicament cartridge including a body having opposed first and second ends, a passage extending through said body through said opposed first and second ends aligned with said inlet and outlet of said housing, a medicament in said passage, and burstable membranes covering said first and second ends of said passage, whereby delivery of fluid under pressure from said pressure actuator through said inlet of said housing ruptures said burstable membranes and delivers said medicament to said outlet of said housing, wherein said delivered medicament has a fine particle fraction of at least 18.5%.

2. The medicament respiratory delivery device as defined in claim 1, wherein said pressure actuator formed between said sheets is collapsible and generally spherical and symmetrical relative to said outlet of said collapsible pressure actuator.

3. The medicament of respiratory delivery device as defined in claim 1, wherein the medicament is albuterol sulfate.

4. The medicament of respiratory delivery device as defined in claim 3, wherein the albuterol sulfate is in the amount of less than 400 μg/dose.

5. The medicament of respiratory delivery device as defined in claim 3, wherein the albuterol sulfate is in the amount of less than 200 μg/dose.

6. The medicament of respiratory delivery device as defined in claim 3, wherein the albuterol sulfate is in the amount of less than 100 μg/dose.

7. A method of delivering a medicament to the respiratory system of a user, comprising the following steps:

providing a medicament respiratory delivery device including a cartridge having opposed inlet and outlet ends, a passage containing medicament extending through said cartridge and through said inlet and outlet ends, a thin burstable membrane having a burst pressure of between 1.2 and 10 atmospheres sealing said passage at said outlet end of said cartridge, and a manually acitivated fluid delivery device communicating with said inlet end of said cartridge; and i activating said manually activated fluid delivery device to deliver fluid under pressure to said inlet end of said cartridge, rupturing said thin burstable membrane, entraining said medicament in said fluid, and delivering said medicament to the respiratory system of the user, wherein said delivered medicament has a fine particle fraction of at least 18.5%.

8. The method of delivering a medicament to the respiratory system of a user as defined in claim 7, wherein the medicament is albuterol sulfate.

9. The method of delivering a medicament to the respiratory system of a user as defined in claim 8, wherein the albuterol sulfate is in the amount of less than 400 μg/dose.

10. The method of delivering a medicament to the respiratory system of a user as defined in claim 8, wherein the albuterol sulfate is in the amount of less than 200 μg/dose.

11. The method of delivering a medicament to the respiratory system of a user as defined in claim 8, wherein the albuterol sulfate is in the amount of less than 100 μg/dose.

* * * * *